US012004878B2

(12) United States Patent
Highsmith et al.

(10) Patent No.: US 12,004,878 B2
(45) Date of Patent: Jun. 11, 2024

(54) COMPOSITE CATHETER WITH SINGLE AXIAL SENSORS AND RING ELECTRODES AND RELATED METHODS

(71) Applicant: BIOSENSE WEBSTER (ISRAEL) LTD., Yokneam (IL)

(72) Inventors: Debby Esther Highsmith, Laguna Niguel, CA (US); Mohammed Ali Pinnjara, Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 942 days.

(21) Appl. No.: 16/503,352

(22) Filed: Jul. 3, 2019

(65) Prior Publication Data

US 2021/0001084 A1    Jan. 7, 2021

(51) Int. Cl.
| | | |
|---|---|---|
| A61M 25/00 | (2006.01) |
| A61B 5/00 | (2006.01) |
| A61B 5/06 | (2006.01) |
| A61B 5/287 | (2021.01) |
| A61B 18/14 | (2006.01) |
| A61M 25/01 | (2006.01) |

(52) U.S. Cl.
CPC ............ *A61B 5/6853* (2013.01); *A61B 5/062* (2013.01); *A61B 5/287* (2021.01); *A61B 5/6857* (2013.01); *A61M 25/0012* (2013.01); *A61M 25/0105* (2013.01); *A61B 18/1492* (2013.01); *A61M 2025/0166* (2013.01); *A61M 2205/0266* (2013.01)

(58) Field of Classification Search
CPC ....... A61B 5/6853; A61B 5/287; A61B 5/062; A61B 5/6857; A61B 5/283; A61B 18/1492; A61M 25/0012; A61M 25/0105; A61M 2025/0166; A61M 2205/0266
See application file for complete search history.

(56) References Cited

U.S. PATENT DOCUMENTS

| | | |
|---|---|---|
| 6,198,974 B1 | 3/2001 | Webster, Jr. |
| 6,484,118 B1 | 11/2002 | Govari |
| 6,987,995 B2 | 1/2006 | Drysen |

(Continued)

FOREIGN PATENT DOCUMENTS

| | | |
|---|---|---|
| EP | 1 876 985 B1 | 1/2008 |
| WO | WO 2004/039273 A2 | 5/2004 |

OTHER PUBLICATIONS

European Search Report dated Nov. 5, 2020, issued in EP Application No. 20183632.7, 9 pages.

*Primary Examiner* — Lindsey G Wehrheim
(74) *Attorney, Agent, or Firm* — Frost Brown Todd LLP (57) ABSTRACT

An electrophysiology catheter includes an elongated support member with shape-memory as a first composite component and an elongated outer tubing as a second composite component, the support member defining a longitudinal axis of the catheter, the support member including a distal portion with a plurality of single-axis sensors, and the elongated outer tubing generally coextensive with the elongated support member, the tubing including a side wall surrounding a lumen through which the support member extends and joins with the outer tubing to form a catheter, the tubing including conductive wires embedded in the side wall and ring electrodes on an outer surface of the side wall, each ring electrode in conductive contact with a respective conductive wire.

17 Claims, 6 Drawing Sheets

(56) References Cited

U.S. PATENT DOCUMENTS

| | | |
|---|---|---|
| 7,142,903 B2 | 11/2006 | Rodriguez et al. |
| 7,274,957 B2 | 9/2007 | Drysen |
| 7,377,906 B2 | 5/2008 | Selkee |
| 7,591,799 B2 | 9/2009 | Selkee |
| 7,593,760 B2 | 9/2009 | Rodriguez et al. |
| 7,720,517 B2 | 5/2010 | Drysen |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,275,440 B2 | 9/2012 | Rodriguez et al. |
| 8,343,076 B2 | 1/2013 | Sela et al. |
| 8,348,888 B2 | 1/2013 | Selkee |
| 8,560,086 B2 | 10/2013 | Just et al. |
| 8,792,962 B2 | 7/2014 | Esguerra et al. |
| 9,037,264 B2 | 5/2015 | Just et al. |
| 9,095,685 B2 | 8/2015 | Sela et al. |
| 2008/0200980 A1 | 8/2008 | Robin et al. |
| 2012/0172703 A1* | 7/2012 | Esguerra ............... A61B 5/062 604/95.04 |
| 2013/0006238 A1* | 1/2013 | Ditter .................. A61B 5/0538 606/41 |
| 2017/0312022 A1 | 11/2017 | Beeckler et al. |
| 2019/0175263 A1* | 6/2019 | Altmann ............ A61M 25/0119 |

\* cited by examiner

COMPOSITE CATHETER WITH SINGLE AXIAL SENSORS AND RING ELECTRODES AND RELATED METHODS

FIELD OF INVENTION

This invention relates to a catheter, in particular, an electrophysiology catheter with location and electrical sensors.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a distal "lasso" structure comprising a generally circular main region generally transverse and distal to the catheter body, where the tubular structure comprises a non-conductive cover over at least the main region of the mapping assembly. A support member including shape-memory is disposed within at least the circular main region of the mapping assembly. A plurality of electrode pairs, each comprising two ring electrodes, are carried by the generally circular main region of the mapping assembly.

More recently, balloon catheter have been put into use to ablate pulmonary vein ostia. A balloon with electrodes on its outer surface is advanced into the left atrium where the balloon is inflated and positioned to nest in an ostium for simultaneous circumferential tissue contact around the ostium. However, depending on the size of the balloon and the ostium, the balloon can be dislodged from the ostium during an ablation procedure.

Conventional methods of assembling a catheter, especially a catheter with sensing components such as ring electrodes and position sensors, can be labor intensive. Moreover, such components are often susceptible to damage and breakage during assembly.

Applicants recognized that there is a need to provide a catheter with a distal "lasso" assembly that can serve as a guidewire and support a balloon nesting in an ostium, while also being capable of sensinge electrical signals from tissue of a tubular region of the ostium and provide location signals for 3-D mapping. Applicants also recognized that there is also a need for a method to construct or assembly a catheter that provides composite components which can be readily assembled.

SUMMARY OF THE DISCLOSURE

In some embodiments, an electrophysiology catheter comprises an elongated support member with shape-memory, defining a longitudinal axis of the catheter, the support member including a distal portion configured with a generally circular portion generally transverse to the longitudinal axis; a single-axis sensor situated on the generally circular portion; and an elongated outer tubing generally coextensive with the support member, the tubing including a side wall surrounding a lumen through which the support member extends, the tubing including a conductive wire embedded in the side wall and a ring electrode on an outer surface of the side wall.

In some embodiments, the elongated support member includes a nitinol wire.

In some embodiments, the generally circular portion is configured for circumferential contact with tissue in a tubular region.

In some embodiments, the support member includes a linear portion proximal of the generally circular portion configured to support a balloon of a second catheter for contact with an ostium of a pulmonary vein.

In some embodiments, the support member includes a generally linear portion proximal of the generally circular portion and the generally linear portion is configured to support a balloon of a second catheter for contact with an ostium of a pulmonary vein while the generally circular portion is in circumferential contact with tissue in the pulmonary vein.

In some embodiments, the ring electrode on the outer tubing includes conductive contact with the embedded conductive wire.

In some embodiments, the outer tubing includes a recess in which the ring electrode includes conductive contact with the conductive wire.

In some embodiments, an electrophysiology catheter comprises an elongated support member with shape-memory, defining a longitudinal axis of the catheter, the support member including a distal portion with a plurality of single-axis sensors; and an elongated outer tubing generally coextensive with the elongated support member, the tubing including a side wall surrounding a lumen through which the support member extends, the tubing including conductive wires embedded in the side wall and ring electrodes on an outer surface of the side wall, each ring electrode in conductive contact with a respective conductive wire.

In some embodiments, the distal portion includes a generally circular portion transverse to the longitudinal axis.

In some embodiments, the elongated support member includes a nitinol wire.

In some embodiments, a method of constructing a catheter comprises providing an elongated support member with shape-memory and a first length, the elongated support member defining a longitudinal axis of the catheter, the support member including a single-axis sensor; providing an elongated outer tubing with a second length coextensive with the first length, the tubing including a side wall surrounding a lumen through which the support member extends, the tubing including a conductive wire embedded in the side wall and a ring electrode on an outer surface of the side wall; and inserting the elongated support member through the lumen of the outer tubing.

In some embodiments, a method of constructing a catheter comprises providing an elongated support member with shape-memory and a first length as a first composite component, the elongated support member defining a longitudinal axis of the catheter, the support member including a distal portion configured with a generally circular portion generally transverse to the longitudinal axis, the generally circular portion including a single-axis sensor; providing an elongated outer tubing with a second length coextensive with the first length as a second composite component, the tubing including a side wall surrounding a lumen through which the support member extends, the tubing including a conductive wire embedded in the side wall and a ring electrode on an outer surface of the side wall; and inserting the elongated support member through the lumen of the outer tubing in assembling the first and second composite components.

In some embodiments, the providing an elongated support member includes forming the single-axis sensor as a wire coil at a location on the generally circular portion and wrapping wires connected to the wire coil around the generally circular portion proximal of the location.

In some embodiments, the providing an elongated support member includes flaring the wires connected to the wire coil before affixing the wires to an elbow portion proximal of the generally circular portion of the elongated support member.

In some embodiments, the wires are affixed to an inner surface of the elbow portion.

In some embodiments, the providing an elongated outer tubing includes extruding the side wall with the conductive wire braided in the side wall.

In some embodiments, the providing an elongated outer tubing includes removing a portion of the side wall to expose the conductive wire and forming a ring electrode in conductive contact with the exposed conductive wire.

In some embodiments, the forming a ring electrode includes applying conductive epoxy includes applying the conductive epoxy to a band area on an outer surface of the outer tubing or mounting a conductive band on the outer tubing.

In some embodiments, the generally circular portion has a length that spans at least 360 degrees.

In some embodiments, the generally circular portion has a length that spans about 450 degrees.

In some embodiments, a center of the generally circular portion is off set from the longitudinal axis.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
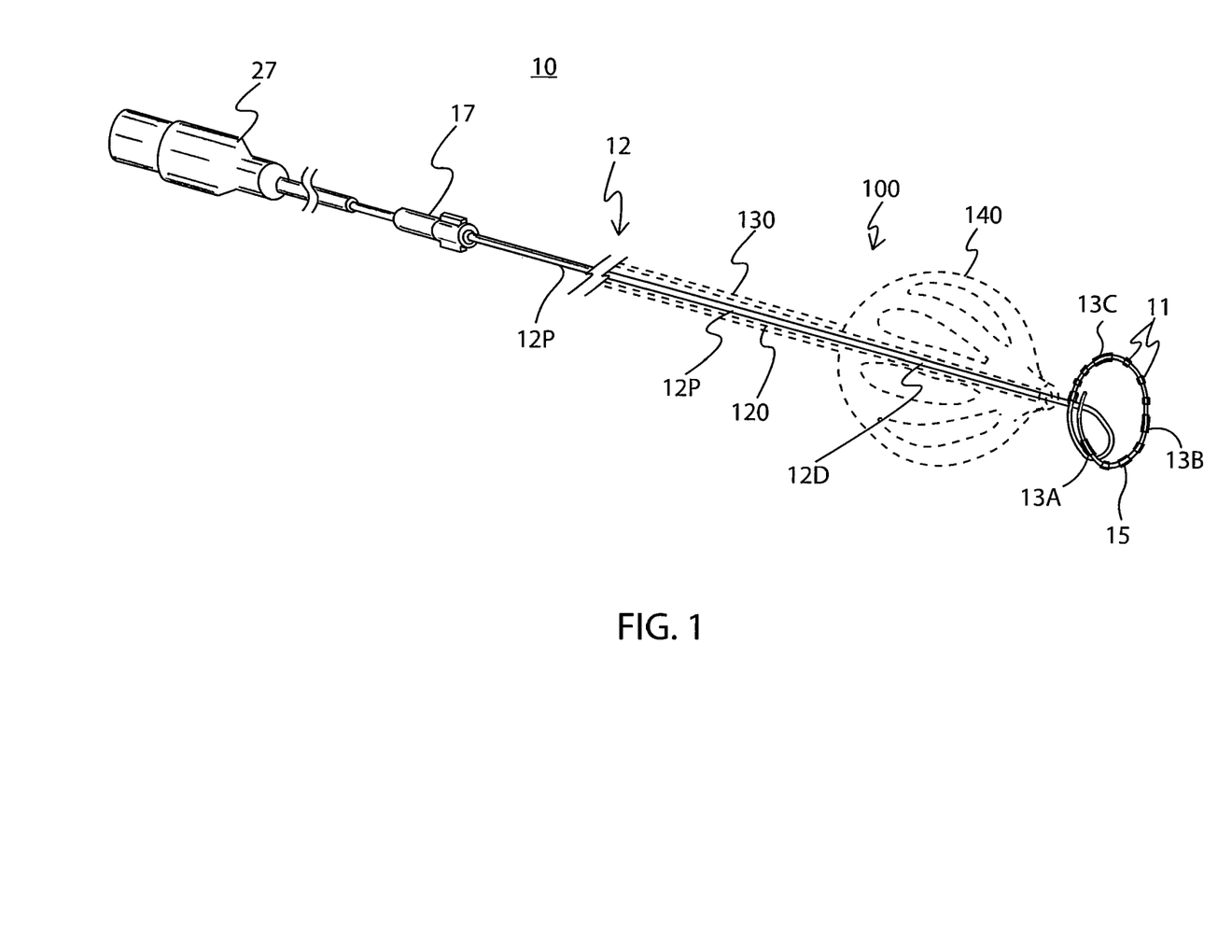
FIG. 1 is a perspective view of a catheter of the present disclosure supporting a balloon catheter, according to one embodiment.
Figure 2:
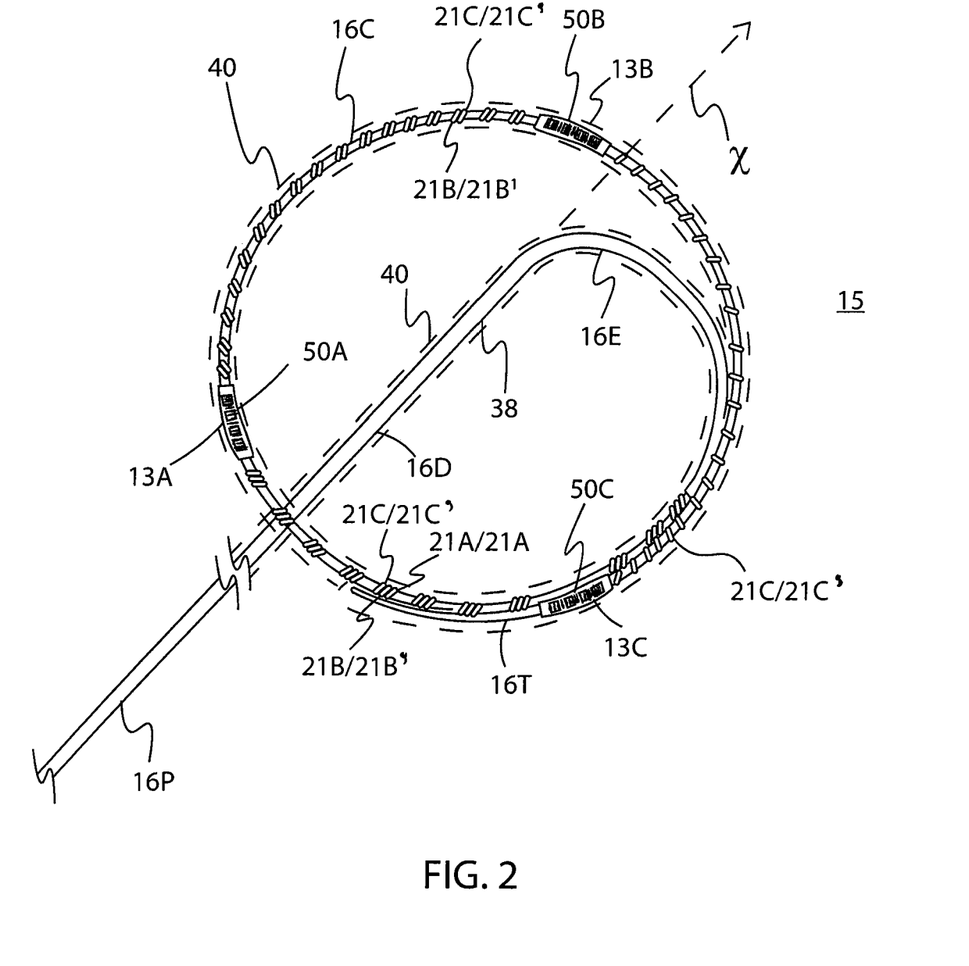
FIG. 2 is an end perspective view of an assembled preformed support member of a distal "lasso" assembly, according to one embodiment.

Referring to FIG. 1 and FIG. 2, embodiments disclosed herein include a catheter 10 that is configured for use with a balloon catheter 100, including an elongated support shaft 12 and a 3-D distal or "lasso" assembly 15. The distal assembly 15 carries one or more single axis sensors ("SASes") 13 configured to be responsive to external magnetic field generators (not shown) for generating signals representative of location of the distal assembly 15, as well as one or more ring electrodes 11 configured for sensing electrical signals from tissue. The distal assembly 15 includes a preformed support member 16 with shape-memory, e.g., a nitinol wire, which provides the 3-D or loop configuration of the distal assembly 15. In that regard, it is understood that in describing the distal assembly 15 the shape-memory elongated support member 16 includes portions that impart shape to corresponding sections of the distal assembly 15, including a curved portion 16C that corresponds with a curved section 15C of the distal assembly 15, and an elbow portion 16E proximal of the curved portion 16C that corresponds with an elbow section 15E of the distal assembly 15. In some embodiments, the curved (e.g., circular, helical or loop, all terms used interchangeably herein) portion 16C of the support member 16 is generally transverse to the shaft 12 that defines a longitudinal axis x of the catheter, and the curved portion 16C has a curved arc or length that spans at least 360 degrees, if not about 450 degrees with a distal overlapping tail portion 16T. Moreover, the curved portion 16C is configured relative to the shaft 12 such that the longitudinal axis x defined by the shaft 12 intersects the curved portion 16C and is offset from a center of a circle generally defined by curved portion 16C.

Figure 3:
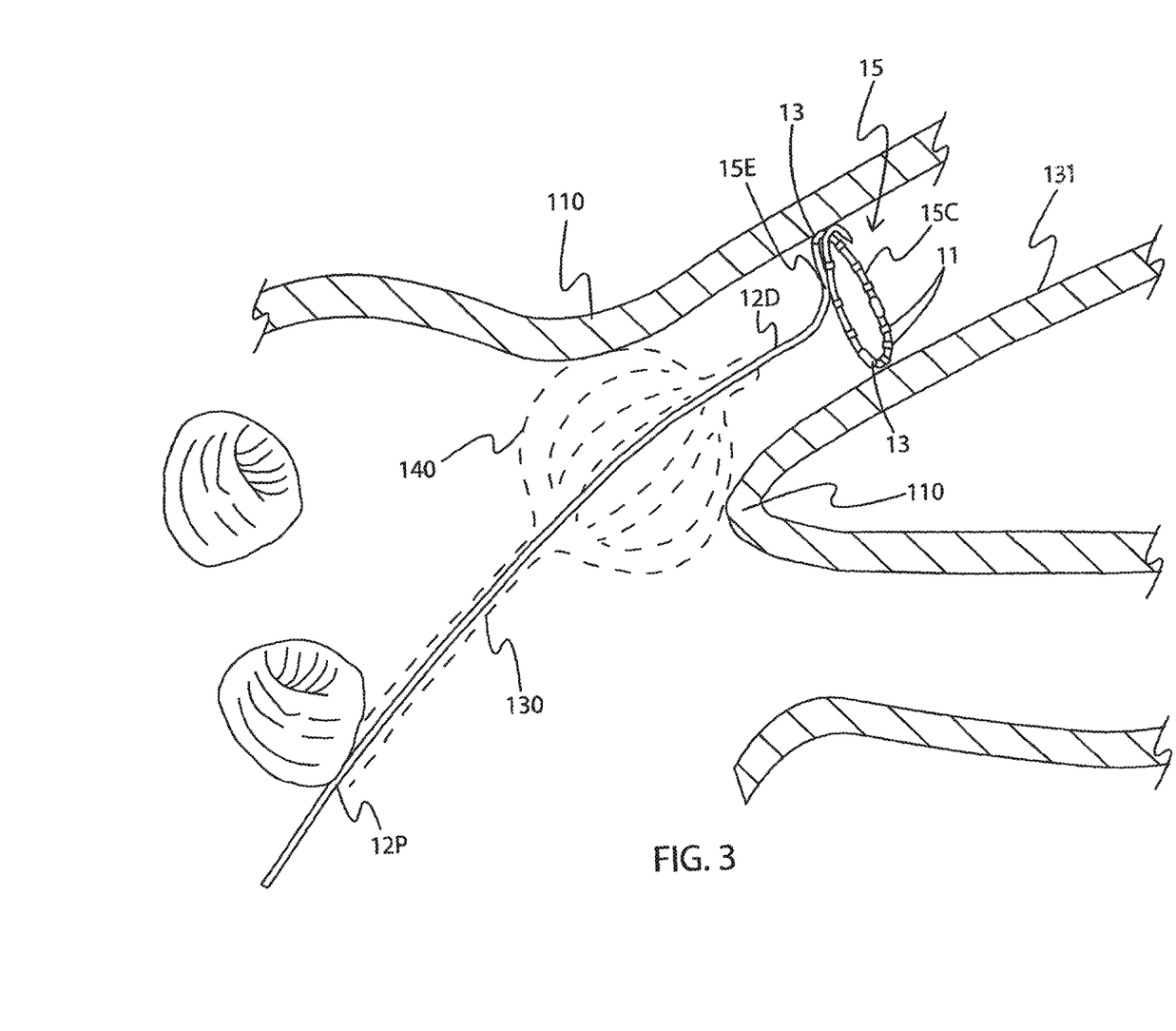
FIG. 3 is a side perspective view of a distal "lasso" assembly situated in a pulmonary vein while supporting a balloon nested in an ostium of the pulmonary vein.

The elongated support shaft 12 of the catheter has a proximal section 12P of lesser flexibility and a distal section 12D of greater flexibility. The shaft 12 is configured to pass through a lumen of a balloon catheter 14 and aptly support the balloon 140 in an ostium 110 of a pulmonary vein 131, as shown in FIG. 3, with the distal lasso assembly 15 extending into the pulmonary vein for circumferential contact with tubular tissue of the pulmonary vein. Advantageously, the proximal section 12P of the shaft is configured with sufficient rigidity to transmit axial pushability and torque imparted by a user, for example, manipulating a connector handle 27 (FIG. 1) at a proximal end of the shaft 12 and a torquer 17 (FIG. 1) mounted on the proximal section 12P, while the distal section 12D of the shaft is configured with sufficient flexibility to accommodate an indirect approach angle between the distal lasso assembly 15 and the ostium 110 in which the supported balloon 140 sits.

In some embodiments, as shown in FIG. 1 and FIG. 2, the shape-memory support member 16 of the distal assembly 15 has an elongated form with a sufficient length to extend through the entirety of the distal assembly 15 and the shaft 12 combined. As such, the elongated support member 16 includes the following:

(i) a longer, generally linear proximal portion 16P, with a first diameter D1, that spans the length of the proximal section 12P of the shaft 12;

(ii) a shorter, generally linear distal portion 16D, with a second diameter D2, that spans the length of the distal section 12D of the shaft 12;

(iii) a distal curved portion 16C, with a third diameter D3, that spans the curved distal section 15C of the distal assembly 15; and (iv) a relatively short elbow portion 16E, with a gradual transitional diameter DT ranging from D2 to D3, that spans the elbow section 15E, extending between the generally linear distal portion 16D and the distal curved section 16C of the support member 16; where diameter D1>diameter D2>diameter D3 such that the proximal portion 16P has the least flexibility, the distal portion 16D has more flexibility and the distal curved portion 16C has the greatest flexibility. In some embodiments, the diameter D1 is about 0.030 inch, the diameter D2 ranges from about 0.014 inch to 0.018 inch and the diameter D3 is about 0.011 inch. Between the proximal portion 16P and the distal portion 16D, the diameter of the wire 16 may have a step transition or a gradual transition between the diameters D1 and D2, as needed or appropriate. Between the distal portion 16D and the curved portion 16C, the elbow portion 16E is configured with a gradual transition between the diameters D2 and D3. In some embodiments, the gradual transition between diameters D2 and D3 occurs in a span of about 2 mm in the elbow portion 16E. The length of the proximal portion 16P of the support member 16 is not critical. However, in some embodiments, the length of the distal portion 16D is at least the longitudinal length of the balloon 140 so it can accommodate the balloon when it is supporting the balloon. In some embodiments, the length of the shaft 12 is about 2 meters, where the distal portion 12D (with the greater flexibility relative to the proximal portion 12P) has a length ranging between about 6 cm and 8 cm.

Figure 4:
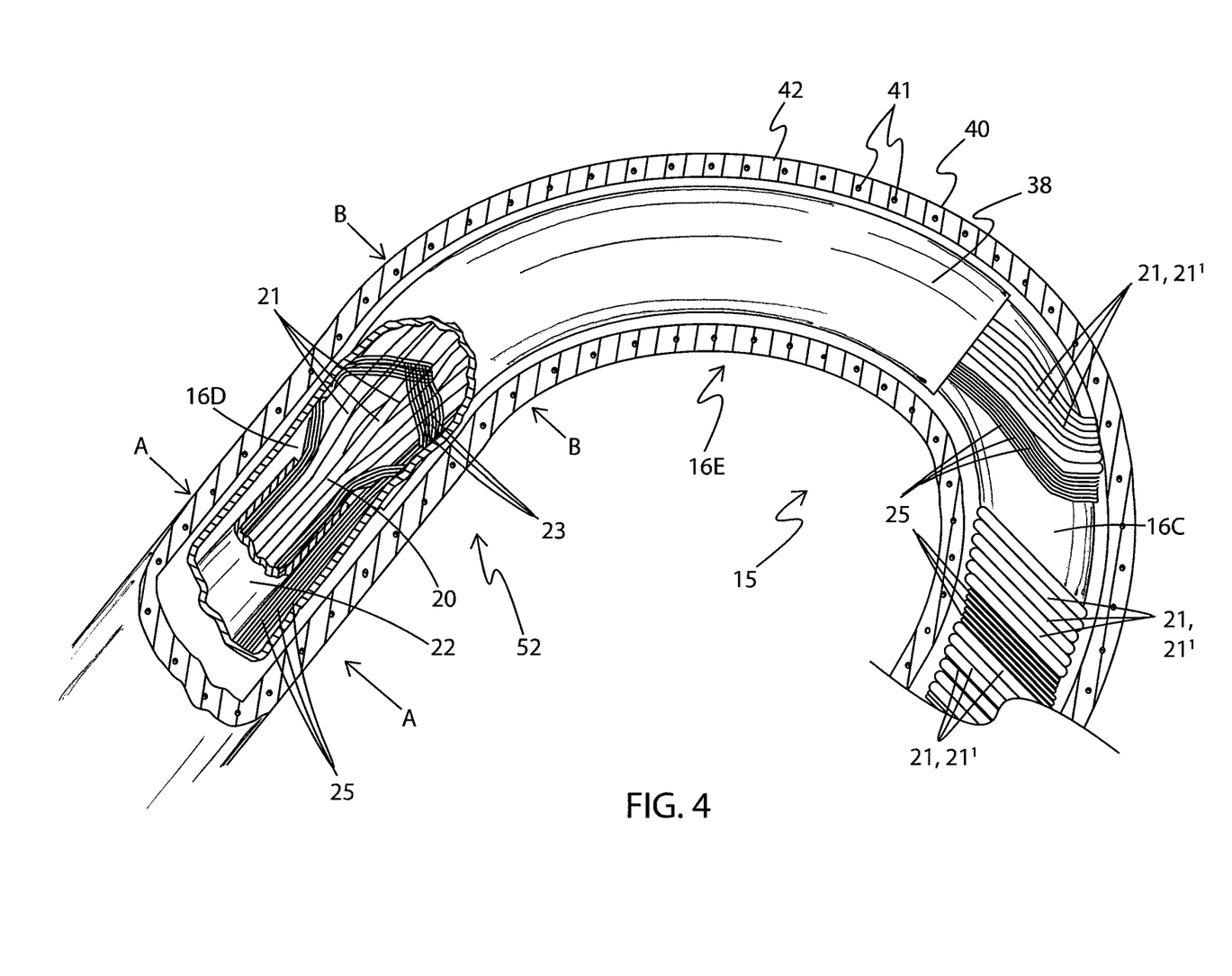
FIG. 4 is a side cross-sectional view of the distal assembly, including an elbow section, according to one embodiment.

With reference to FIG. 2 and FIG. 4, the distal curved portion 16C of the shape-memory support member 16 carries one or more SASes. It is understood that each SAS 13 has a respective wire coil sensor 50 and a cable 20, where the wire coil sensor 50 is wrapped around a selected location on the distal curved portion 16C and the cable 20 includes a dedicated pair of wires 21, 21' that are encased along with shielding fibers 23 within an insulating sheath 22 generally coextensive with the wires 21, 21'. For simplicity in the description provided herein, wires 21, 21' of all SASes 13 carried on the distal assembly 15 are illustrated herein as passing through one common insulating sheath 22 with shared shielding fibers 23 in forming a single cable 20 for all SASes 13.

In the illustrated embodiment of FIG. 2, the distal assembly 15 carries three SASes, namely, proximal SAS 13A, middle SAS 13B and distal SAS 13C, including three wire coils 50A, 50B and 50C, referred to herein respectively as the proximal coil, the mid coil and the distal coil, that are arranged in equi-angular positions about the curved portion 16C, e.g., at about 0, 120 and 240 degrees. The wire coil 50 of each SAS is connected to a dedicated pair of wires 21 and 21', with the wire 21 connected to a distal end of the wire coil 50 and the wire 21' connected to a proximal end of the wire coil 50. Thus, in the illustrated embodiment, the middle wire coil 50B (best shown in FIG. 6) is connected to wire pair 21C and 21C', the mid coil 50B is connected to wire pair 21B and 21B' and the proximal coil 50A is connected to wire pair 21A and 21A'. To assemble the SASes 13A, 13B and 13C on the curved portion 16C of the preformed support member 16, a method making or assembling a preformed support member with SASes in some embodiments includes (i) wrapping the wire coil 50C on the preformed support member 16 at location 240 degrees to form SAS 13C, (ii) connecting the wire pair 21C and 21C' to the distal and proximal ends, respectively, of the wire coil 50C, and (iii) wrapping the wire pair 21C and 21C' around the curved portion 16C in a proximal direction. Different wrapping patterns may be employed to provide strain relief against wire breakage during use of the catheter.

The method of assembling also includes (iv) wrapping the wire pair 21C and 21C' at location 120 degrees, (v) wrapping the wire coil 50B over the wrapped wire pair 21C and 21C' to form SAS 13B, (vi) connecting the wire pair 21B and 21B' to the distal and proximal ends, respectively, of the wire coil 50B, and (vi) wrapping the wire pairs 21C and 21C' and 21B and 21B' around the curved portion 16D in a proximal direction.

The method of assembling further includes (vii) wrapping the wire pairs 21C and 21C' and 21B and 21B' at location 0 degrees, (viii) wrapping the wire coil 50A over the wrapped wire pairs 21C and 21C' and 21B and 21B' to form SAS 13A, (ix) connecting the wire pair 21A and 21A' to the distal and proximal ends, respectively, of the wire coil 50A, and (x) wrapping the wire pairs 21C and 21C', 21B and 21B', and 21A and 21A' around the curved portion 16C in a proximal direction. It is understood that one or more heat shrink sleeves may be over the formed SASes and the wrapped wire pairs between adjacent SASes.

It is also understood that the sequence of the actions recited above or the direction of wrapping (e.g., distal to proximal or proximal to distal) may be varied, as desired or appropriate and that a heat shrink sleeve can be placed over each SAS, the wire coils or wrapped wire pair(s) beneath the wire coils, as desired or appropriate. In any case, the distal SAS 13C includes the wire coil 50C with its distal end connected to the wire 21C and its proximal end connected to the wire 21C', the mid SAS 13B includes the wire coil 50B with its distal end connected to the wire 21B and its proximal end connected to the wire 21B', where the wire coil 50B is coiled over the wires 21C and 21C', and the proximal SAS 13A includes the wire coil 50A with its distal end connected to the wire 21A and its proximal end connected to the wire 21A', where the wire coil 50A is coiled over the wires 21C and 21C' and 21B and 21B'.

Figure 5A:
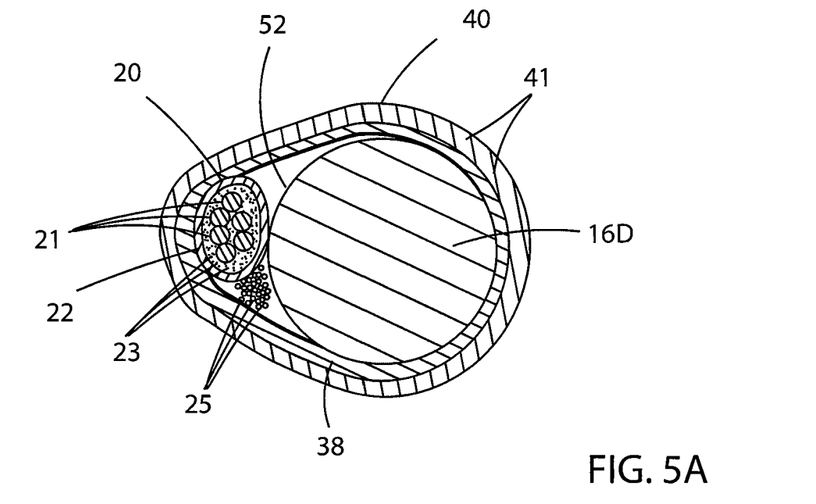
FIG. 5A is an end cross-sectional view of the distal assembly of FIG. 4, taken along line A-A.
Figure 5B:
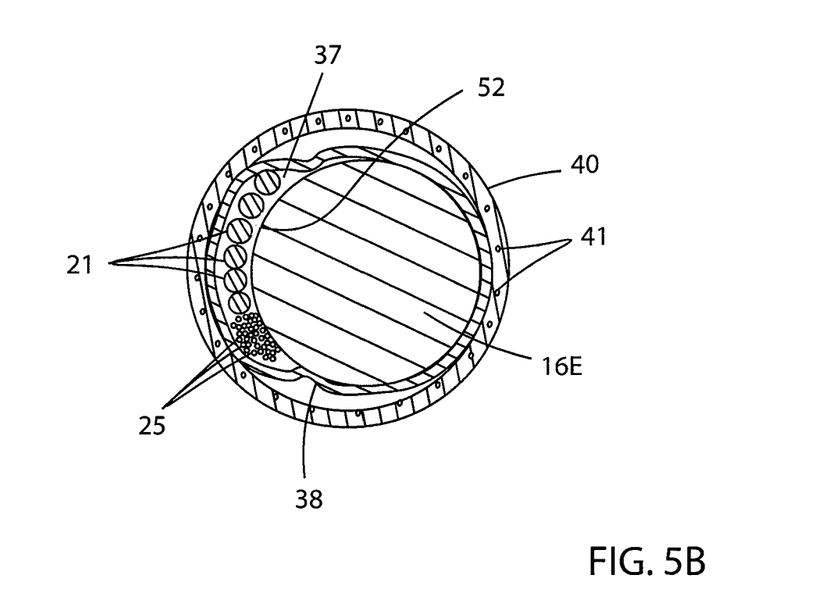
FIG. 5B is an end cross-sectional view of the distal assembly of FIG. 4, taken along line B-B.

At the elbow portion 16E, the cable 20 housing the wire pairs 21 (e.g., 21A, 21A', 21B, 21B', 21C and 21C') advantageously lies on an inside surface 52 (inward facing toward the curvature) of the elbow portion 16E in minimizing the outer diameter of the distal assembly 15 in that region, as better shown in FIG. 4, FIG. 5A and FIG. 5B. In that regard, the distal end of the insulating sheath 22 of the cable 20, and the shielding fibers 23 therein are cut or otherwise terminated proximal of the elbow portion 16E to expose the various wire pairs 21. Moreover, all of the wires 21 are spread or fanned out, laid against the inside surface 52, and affixed by an adhesive 37 (FIG. 5B) to minimize the circumferential size and profile of the distal assembly 15 at its elbow portion 15E. The distal end portions of the shield fibers 23 may be wrapped around the wires 21 and the preformed support member 16 (FIG. 4) to encircle them for a tighter profile around the preformed support member 16. A heat shrink sleeve 38 may extend over the cable 20 and the shielding fibers 23 proximal of the elbow portion 16E, and the exposed wires 21 and safety fibers 25 in the elbow portion 16E. Proximal and terminal ends of the heat shrink sleeve may be at any location along the support member 16, as needed or appropriate.

Accordingly, the method of assembling the preformed support member 16 with the SASes, includes (i) preparing the cable 20 for affixation to an elbow portion 16E; and (ii) affixing the prepared cable to the elbow portion, wherein the preparing the cable includes: (a) cutting or terminating a distal end of the outer insulating sheath 22 generally proximal of the elbow portion; (b) exposing the wires 21 in the cable; (c) spreading or fanning out the exposed wires 21, and wherein the affixing the prepared cable includes: (a) laying the fanned out exposed wires onto an inside surface 52 of the elbow portion; (b) applying adhesive to the fanned out exposed wires 21 on the inside surface of the elbow portion; and (c) covering the affixed exposed wires and at least a distal portion of the insulating sheath 22 with a heat shrink sleeve. The preparing the cable may also include cutting or terminating distal ends of the shielding fibers 23, and wrapping the distal ends around the exposed wires 21 and the preformed support member 16. The affixing the prepared cable may also include covering a plurality of safety strands 25 (e.g., VECTRAN strands) whose proximal ends are anchored to the shaft 12 and whose lengths are coextensive with the wires 21 under the heat shrink sleeve 38 to tether the distal assembly 15 to the shaft 12 as a safety measure against detachment of the distal assembly 15. Distal ends of the safety strands 25 may be anchored to a distal end of the preformed support member 16. A description of suitable SASes is provided in U.S. Pat. No. 8,792,962, the entire content of which is hereby incorporated by reference.

Figure 6:
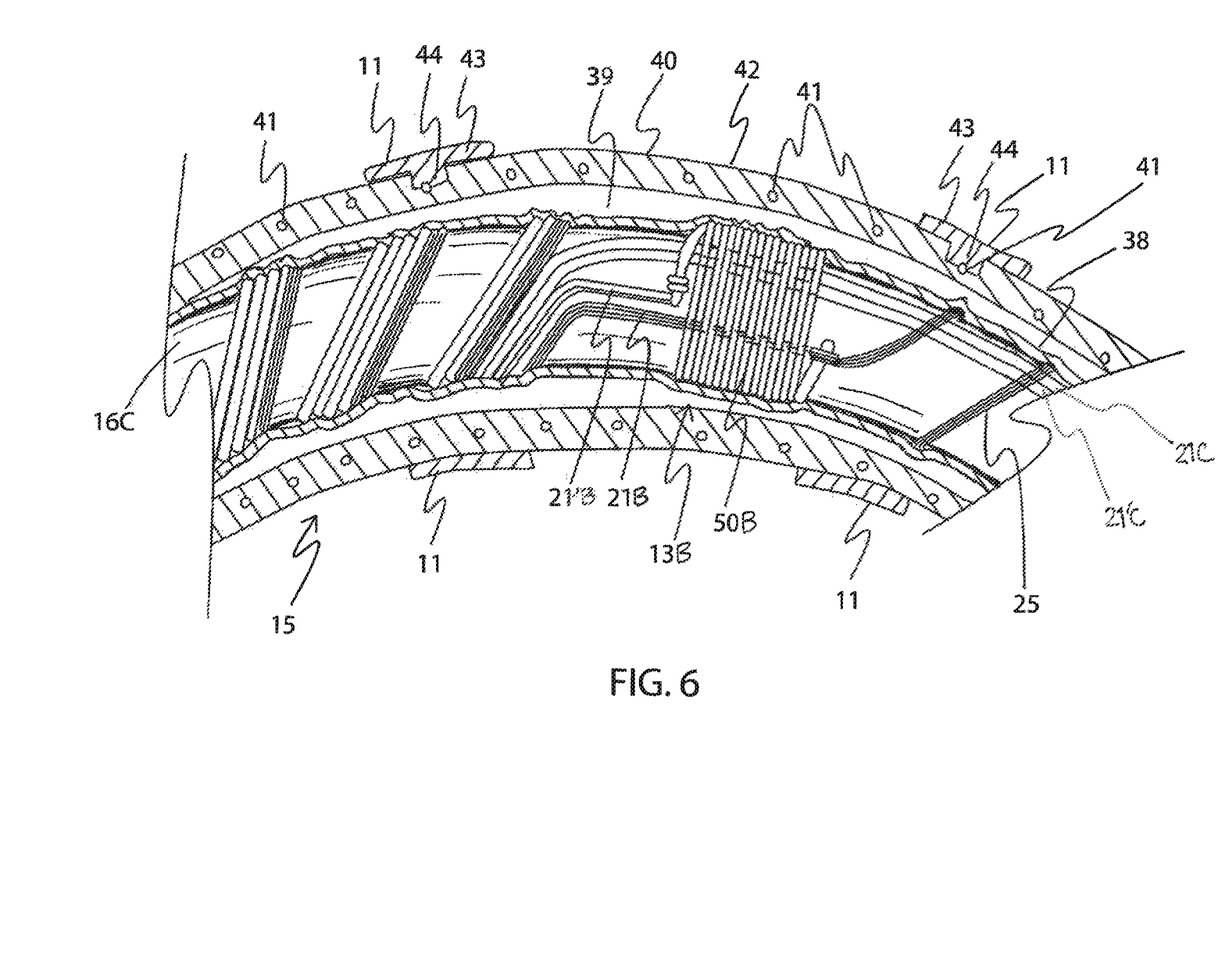
FIG. 6 is a side cross-sectional view of the distal assembly, including a generally circular section, according to one embodiment.

As previously mentioned, the distal assembly 15 not only carries one or more SASes 13, it also carries one or more ring electrodes 11. As shown in FIG. 6, the distal assembly 15 includes an outer braided tubing 40 that has the ring electrodes 11 and conductive lead wires 41. Although the tubing 40 has a lumen 39, the conductive wires 41 are embedded in the side wall 42 as part of an extrusion manufacturing process of the tubing 40, as understood by one or ordinary skill in the art. In some embodiments, the outer braided tubing 40 covers the entire length of the preformed support structure 16, including the proximal portion 16P, the distal portion 16D, the elbow portion 16E, and the curved portion 16C. Of the portion of the braided tubing 40 that covers the curved portion 16C, the ring electrodes 11 carried thereon are formed by selective removal, e.g., laser cutting, of the outer side wall 42 to form recesses 44 at predetermined locations so as to expose selected individual wires 41. Conductive epoxy 43, for example, platinum conductive epoxy or gold conductive epoxy, is then applied to fill the recesses 44 and also along the circumference at the recess around the exterior of the side wall 42 to form a respective ring electrode 11 at each of the predetermined locations. Extruding the tubing 40 with the wires 41 may be accomplished with conventional wire extrusion machines. Braided wires 41 embedded in the side wall 42 of the tubing 40 may extend distal of their respective ring electrodes without any adverse impact on the function of the ring electrodes. It is understood that the ring electrode 11 may also be formed with use of conductive bands that are mounted on the tubing 40 to surround the tubing circumferentially at each recess 44. Thus, a method of constructing an outer tubing 40 with ring electrodes 11 and embedded lead wires 41 includes: (i) extruding a tubing 40 with wires 41 embedded in side wall 42, where the tubing has an outer surface, and an inner surface defining a lumen; (ii) removing a portion of the side wall from the exterior surface to expose a wire 41 within a recess; (iii) forming a ring electrode around the outer surface, including applying conductive epoxy to fill the recess and a corresponding circumferential band around the recess to form a ring electrode 11 or mounting a conductive band on the tubing at the location of recess.

After the outer tubing 40 has been constructed with the ring electrodes 11 and the embedded wires 41, the outer tubing 40 can be slipped on over the assembled distal assembly 15. In some embodiments, a method of assembling includes: (i) the above-described method of making or constructing the outer tubing 40 with the ring electrodes 11 and embedded wires 41; (ii) the above-described method of assembling the preformed support member 16 with the SASes 13; and (iii) mounting the constructed outer tubing 40 onto the preformed support member 16 with the SASes 13. Mounting may be accomplished by inserting the assembled preformed support member 16 into the lumen 39 of the constructed outer tubing 40. As such, the construction of the catheter 10 is simplified by compartmentalization into construction of the outer tubing 40 which provides the ring electrodes, and construction of the underlying SAS-carrying support member 16. Distal ends of the outer tubing 40 and the support structure 16 may be jointly plugged and sealed with a ball of sealant, e.g., polyurethane, to form an atraumatic bulbous distal end of the catheter 10.

At the proximal end of the outer tubing 40 terminating near or in the connector handle 27, proximal portions of the wires 41 may be exposed from the tubing 40 by selective removal of the side wall 42 for connection to suitable electrical terminals in the connector handle 27 in the transmission of sensed electrical signals to an electrophysiology workstation for processing, as known in the art. The cable 20 (including the wire pairs 21, 21' of each SAS carried on the distal assembly 15) extends through the lumen 39 of the outer tubing 40, coextensively with the distal and proximal portions 16D and 16P of the support member 16, in passing through the shaft 12 of the catheter and into the connector handle 27 in the transmission of location signals to the electrophysiology workstation for processing, as known in the art.

In use, the catheter 10 is fed into and through a lumen 120 of the balloon catheter 100, where the lumen 120 extends through a shaft 130 of the balloon catheter and the balloon 140 itself. To feed the distal assembly 15, it is straightened so that the curved portion 15C first enters the lumen 120 followed by the elbow 15E, and so forth. The distal assembly 15 is advanced relative to the balloon catheter until the distal assembly 15 passes the distal end of the balloon catheter, upon which the distal assembly 15 is free to assume the 3-D shape in the patient's left atrium pursuant to its underlying preformed shape-memory support member 16. The catheter 10 is then maneuvered so as to insert the distal assembly 15 into a pulmonary vein where the ring electrodes 11 are in contact with tissue along an inner circumference of tubular region of the pulmonary vein. Using the shaft 12 and particularly the distal section 12D as a guidewire, the balloon catheter 100 is then advanced toward the ostium of the pulmonary vein until a distal surface of the balloon comes into contact with the ostium. The shaft 12 of the catheter 10 has a less flexible proximal section 12P so as to function as a guidewire for the balloon catheter 100 and a more flexible distal section 12D so as to allow flexure where the approach angle of the distal assembly 15 is not in alignment with the center of the ostium, yet have sufficient rigidity to aptly support the balloon thereon. The one or more SASes 13 in the distal assembly 15 respond to external magnetic field generators typically located under the patient's bed to provide location signals, and the ring electrodes 11 carried on the distal assembly 15 sense electrical signals from the tissue of the pulmonary vein, including electrical signals to assess whether PV isolation has been achieved by ablation of tissue of or adjacent the ostium.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. It is understood that a feature of the present invention is applicable to multiplying linear motion of a puller wire, contraction wire, or any other object requiring insertion, removal, or tensioning within a medical device, including the disclosed electrophysiology catheter. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter, comprising:
    an elongated support member with shape-memory, defining a longitudinal axis of the catheter, the support member including a distal portion configured with a generally circular portion generally transverse to the longitudinal axis, and an elbow portion proximal of the generally circular portion, the elbow portion having an inside surface facing inwardly of the generally circular portion;
    a single-axis sensor situated on the generally circular portion, the sensor including a coil, a first wire and a second wire, the coil wound on the elongated support member, the coil having a distal end and a proximal end, the first wire having a distal end and a proximal portion, the second wire having a distal end and a proximal portion, the distal end of the first wire connected to the proximal end of the coil, the distal end of the second wire connected to the distal end of the coil, the first and second wires extending from the coil extend along the inside surface of the elbow portion;
    an elongated outer tubing generally coextensive with the support member, the tubing including a side wall surrounding a lumen through which the support member extends, the tubing including a conductive wire embedded in the side wall and a ring electrode on an outer surface of the side wall; and
    an insulating sheath circumferentially surrounding at least the first and second wires, the insulating sheath having a distal end terminating proximal of the elbow portion such that the first and second wires are fanned out along the inside surface of the elbow portion distal of the distal end of the insulating sheath.

2. The catheter of claim 1, wherein the elongated support member includes a nitinol wire.

3. The catheter of claim 1, wherein the generally circular portion is configured for circumferential contact with tissue in a tubular region.

4. The catheter of claim 1, wherein the support member includes a linear portion proximal of the generally circular portion configured to support a balloon of a second catheter for contact with an ostium of a pulmonary vein.

5. The catheter of claim 1, wherein the support member includes a generally linear portion proximal of the generally circular portion and the generally linear portion is configured to support a balloon of a second catheter for contact with an ostium of a pulmonary vein while the generally circular portion is in circumferential contact with tissue in the pulmonary vein.

6. The catheter of claim 1, wherein the ring electrode on the outer tubing includes conductive contact with the embedded conductive wire.

7. The catheter of claim 1, wherein the outer tubing includes a recess in which the ring electrode includes conductive contact with the conductive wire.

8. The catheter of claim 1, further comprising a safety strand coextensive with the first and second wires in at least the elbow portion.

9. The catheter of claim 1, further comprising a shielding fiber coextensive with the first and second wires, with a distal end terminating proximal of the elbow portion.

10. A method of constructing a catheter, comprising:
    providing an elongated support member with shape-memory and a first length, the elongated support member defining a longitudinal axis of the catheter, the support member including a single-axis sensor;
    providing an elongated outer tubing with a second length coextensive with the first length, the tubing including a side wall surrounding a lumen through which the support member extends, the tubing including a conductive wire embedded in the side wall and a ring electrode on an outer surface of the side wall; and
    inserting the elongated support member through the lumen of the outer tubing;
    wherein the providing an elongated support member includes forming the single-axis sensor as a wire coil at a location on the generally circular portion and wrapping wires connected to the wire coil around the generally circular portion proximal of the location;
    wherein the providing an elongated support member includes fanning out the wires connected to the wire coil before affixing the wires to an elbow portion proximal of the generally circular portion of the elongated support member.

11. The method of claim 10, wherein the wires are affixed to an inner surface of the elbow portion.

12. The method of claim 10, wherein the providing an elongated outer tubing includes extruding the side wall with the conductive wire braided in the side wall.

13. The method of claim 10, wherein the providing an elongated outer tubing includes removing a portion of the side wall to expose the conductive wire and forming a ring electrode on the outer tubing in conductive contact with the exposed conductive wire.

14. The method of claim 13, wherein the forming a ring electrode includes applying a conductive epoxy to a band area on an outer surface of the outer tubing to form the ring electrode.

15. The method of claim 10, wherein the generally circular portion has a length that spans at least 360 degrees.

16. The method of claim 10, wherein the generally circular portion has a length that spans about 450 degrees.

17. The method of claim 10, wherein a center of the generally circular portion is off set from the longitudinal axis.

* * * * *